| (12) | United States Patent | (10) Patent No.: | US 8,097,863 B2 |
|---|---|---|---|
| | Yamazoe | (45) Date of Patent: | Jan. 17, 2012 |

(54) MODE-LOCKED LASER DEVICE, PULSED LASER LIGHT SOURCE DEVICE, MICROSCOPE DEVICE

(75) Inventor: Shogo Yamazoe, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 197 days.

(21) Appl. No.: 12/507,490

(22) Filed: Jul. 22, 2009

(65) Prior Publication Data

US 2010/0038558 A1     Feb. 18, 2010

(30) Foreign Application Priority Data

Aug. 12, 2008  (JP) ................................. 2008-207582

(51) Int. Cl.
*G01N 21/64*     (2006.01)
*H01S 3/00*      (2006.01)

(52) U.S. Cl. ......... 250/458.1; 359/385; 372/11; 372/16; 372/18

(58) Field of Classification Search .................. 359/385; 372/11, 16, 18; 250/458.1
See application file for complete search history.

(56) References Cited

U.S. PATENT DOCUMENTS

| 5,163,059 | A | * | 11/1992 | Negus et al. .................... 372/18 |
| 5,703,900 | A | | 12/1997 | Nozaki et al. |
| 5,815,519 | A | * | 9/1998 | Aoshima et al. ................ 372/25 |
| 5,848,092 | A | * | 12/1998 | Mitsumoto et al. ........... 372/107 |
| 6,560,267 | B1 | * | 5/2003 | Tomaru et al. .................. 372/98 |
| 2002/0180965 | A1 | * | 12/2002 | Engelhardt et al. ........... 356/318 |

FOREIGN PATENT DOCUMENTS

| JP | 3378103 B2 | 2/2003 |
| JP | 3450073 B2 | 9/2003 |

OTHER PUBLICATIONS

Vincent Le Flanchec, et al. "A Phased-Locked S.A.M Mode-Locked Laser for the ELSA Photoinjector", Proceedings of EPAC, 2006, pp. 3164-3166, vol. THPCH158, Edinburgh, Scotland.

* cited by examiner

*Primary Examiner* — David Porta
*Assistant Examiner* — Hugh H Maupin
(74) *Attorney, Agent, or Firm* — Sughrue Mion, PLLC

(57) ABSTRACT

There is provided a mode-locked laser including: a resonator having a pair of resonance mirrors; a solid-state laser medium, disposed in the resonator and outputting oscillating light due to excitation light being incident thereon; an excitation unit that causes the excitation light to be incident on the solid-state laser medium; a mode-locked element, disposed in the resonator for inducing mode locking; and a temperature adjusting unit that adjusts the temperature of the pair of resonance mirrors such that oscillating light of a specific frequency is output from the resonator.

10 Claims, 10 Drawing Sheets

MODE-LOCKED LASER DEVICE, PULSED LASER LIGHT SOURCE DEVICE, MICROSCOPE DEVICE

CROSS-REFERENCE TO RELATED APPLICATION

This application is based on and claims priority under 35 USC 119 from Japanese Patent Application No. 2008-207582 filed on Aug. 12, 2008, the disclosure of which is incorporated by reference herein.

BACKGROUND

1. Technical Field

The present invention relates to a mode-locked laser device, a pulsed laser light source device, and a microscope device. In particular the present invention relates to a resonator length adjustable mode-locked laser device, and a pulsed laser light source device and microscope device of the same.

2. Related Art

Recently, in many industries and academic disciplines, such as optical communication and optical data processing, applications of ultra high speed optical signals in picosecond and femtosecond ranges are rapidly expanding, and demand for devices that generate such ultra high speed optical signals has increased. The most basic form of such ultra high speed optical signals is a light pulse of extremely short duration width, and it is known that if such an ultra short light pulse can first be obtained, then this can be converted into other signal forms by derivation therefrom.

Currently, as methods for generating ultra short light pulses, the method that can generate light pulses with the shortest duration width and the highest pulse repetition rate, stably, is a method of pulse generation actuation arising from a nonlinear optical effect of a laser light source itself. This type of pulse generation actuation is generally referred to as passive mode locking, or self-mode locking. In comparison to these methods there are also pulse generation actuation by application of an external modulating signal to a laser light source, these being referred to as active mode locking or forced mode locking.

In all the pulse generation actuations the pulse repetition rate of the light pulse is in an inverse relationship to the cycle time of the laser resonator. The cycle time of the laser resonator is determined by the length of the laser resonator, and the length of the laser resonator drifts with changes in temperature, or changes by fluctuating with vibrations.

Technology has therefore been proposed to avoid changes in the laser resonator length due to the surrounding temperature (see, for example, Japanese Patent Nos. 3378103 and 3450073).

When applying an ultra short light pulse generated by an light pulse laser light source device, in many cases fluctuations in the pulse repetition rate of the light pulse are undesirable. For example, when constructing a measuring system using light pulses, since the obtainable time resolution depends on the precision of pulse locking, when there is jitter due to fluctuations in the pulse repetition rate then this is detrimental to the time resolution. In such cases, the shortness of duration width corrupts and becomes meaningless. Consequently, up to now the pulse repetition rate of generated light pulses has been stabilized by controlling the resonator length in a passive mode-locked laser device.

As methods for controlling conventional resonator lengths there are methods in which one mirror configuring a resonator is fixed to a stage movable by motor driving, and a the second mirror thereof is fixed to a piezo element. The pulse repetition rate is adjusted therein by course adjustment of the resonator length by motor driving the first mirror, and then fine adjustment is performed by driving the second mirror with the piezo element. There is, for example, description in the following publication:

"Proceeding of EPAC 2006, Edinburgh, Scotland THPCH158 p. 3164".

However, when frequency control is performed using a movable stage and piezo element, the construction of the device becomes complicated, and since driving drivers of movable stages and piezo elements are high cost, the cost of the device becomes high.

SUMMARY

The present invention is made in consideration of the above circumstances and an objective thereof is to provide a mode-locked laser device in which the pulse repetition rate of the pulse light can be readily adjusted with a simple and compact structure, and a pulsed laser light source device and microscope device of the same.

In order to achieve the above objective, an aspect of the present invention provides a mode-locked laser including:

a resonator having a pair of resonance mirrors;

a solid-state laser medium, disposed in the resonator and outputting oscillating light due to excitation light being incident thereon;

an excitation unit that causes the excitation light to be incident on the solid-state laser medium;

a mode-locked element, disposed in the resonator for inducing mode locking; and a temperature adjusting unit that adjusts the temperature of the pair of resonance mirrors such that oscillating light of a specific frequency is output from the resonator.

According to the invention, the pulse repetition rate of pulse light output from the resonator is adjusted by changing the resonator length by adjusting the temperature of the pair of resonance mirrors using the temperature adjusting unit. The pulse repetition rate of the pulse light can thereby be readily adjusted with a simple and compact structure.

The pair of resonance mirrors may also be retained by the same retaining member, and the temperature adjusting unit may adjust the temperature of the retaining member.

Also, configuration may be made wherein the mode-locked element is a semiconductor saturable absorber mirror device making common usage of one resonance mirror of the pair of resonance mirrors.

In addition, configuration may be made wherein: a group velocity dispersion compensation unit is provided in the resonator, the group velocity dispersion compensation unit controlling the group velocity dispersion in the resonator; and the resonator induces soliton mode-locked.

In addition, configuration may be made wherein: the mode-locked element is formed from a medium that induces an optical Kerr effect and makes common usage of the solid-state laser medium; and the resonator induces Kerr lens mode locking.

In addition, configuration may be made provided with a pulse repetition rate detection unit that detects the pulse repetition rate of pulse light output from the resonator, wherein the temperature adjusting unit adjusts the temperature of the pair of resonance mirrors such that the difference between the pulse repetition rate detected by the pulse repetition rate detection unit and the specific pulse repetition rate is minimized.

Further, another aspect of the present invention provides a pulse laser light source device including:

a plurality of mode-locked laser devices; and a plurality of detecting units that detect respective pulse lights output from respective of the plurality of mode-locked laser devices, wherein each of the plurality of mode-locked laser devices includes:

a resonator having a pair of resonance mirrors;

a solid-state laser medium, disposed in the resonator and outputting oscillating light due to excitation light being incident thereon;

an excitation unit that causes the excitation light to be incident on the solid-state laser medium;

a mode-locked element, disposed in the resonator for inducing mode locking; and a temperature adjusting unit that adjusts the temperature of the pair of resonance mirrors such that oscillating light of a specific frequency is output from the resonator, and wherein the temperature adjusting unit of at least one mode-locked laser device from the plurality of mode-locked laser devices adjusts the temperature of the pair of resonance mirrors such that a difference in pulse separation between the plurality of pulse lights detected by the plurality of detection units is minimized.

According to this aspect of the invention, a stable, compact and low cost pulsed laser light source device with variable pulse repetition rate can be realized.

According to this aspect of the invention, a compact microscope device employing coherent anti-Stokes Raman scattering can be realized.

According to the present invention, as explained above, the excellent effect is exhibited in that the pulse repetition rate of pulse light can be readily adjusted with a simple, compact and low cost configuration.

BRIEF DESCRIPTION OF THE DRAWINGS

Exemplary embodiments of the present invention will be described in detail based on the following figures, wherein.

DETAILED DESCRIPTION

Explanation will now be given of details of exemplary embodiments of the present invention, with reference to the figures.

First Exemplary Embodiment

Explanation will first be given of a first exemplary embodiment of the present invention.

Figure 1A:
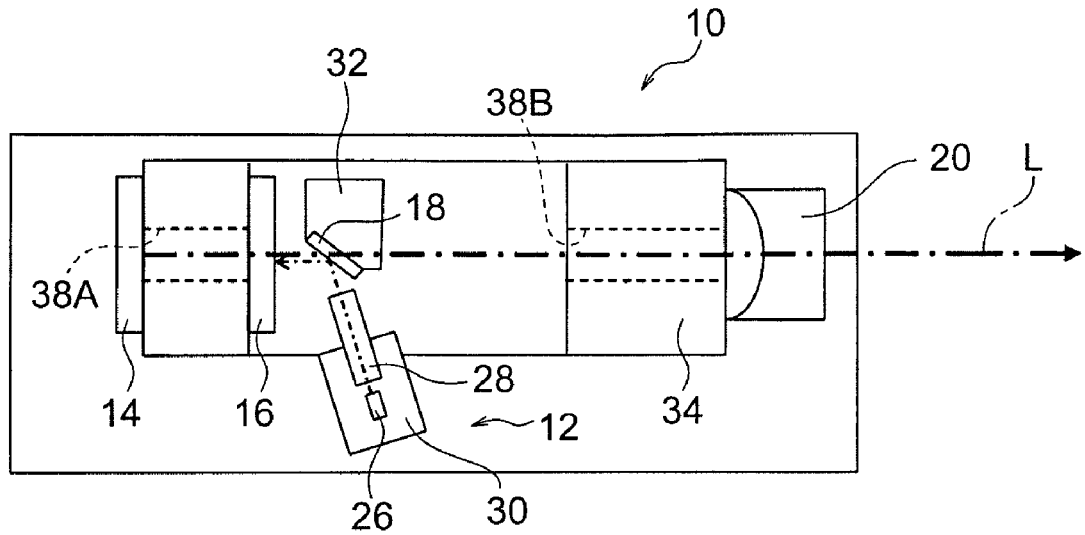
FIG. 1A is a schematic configuration diagram of a mode-locked laser device according to a first exemplary embodiment.
Figure 1B:
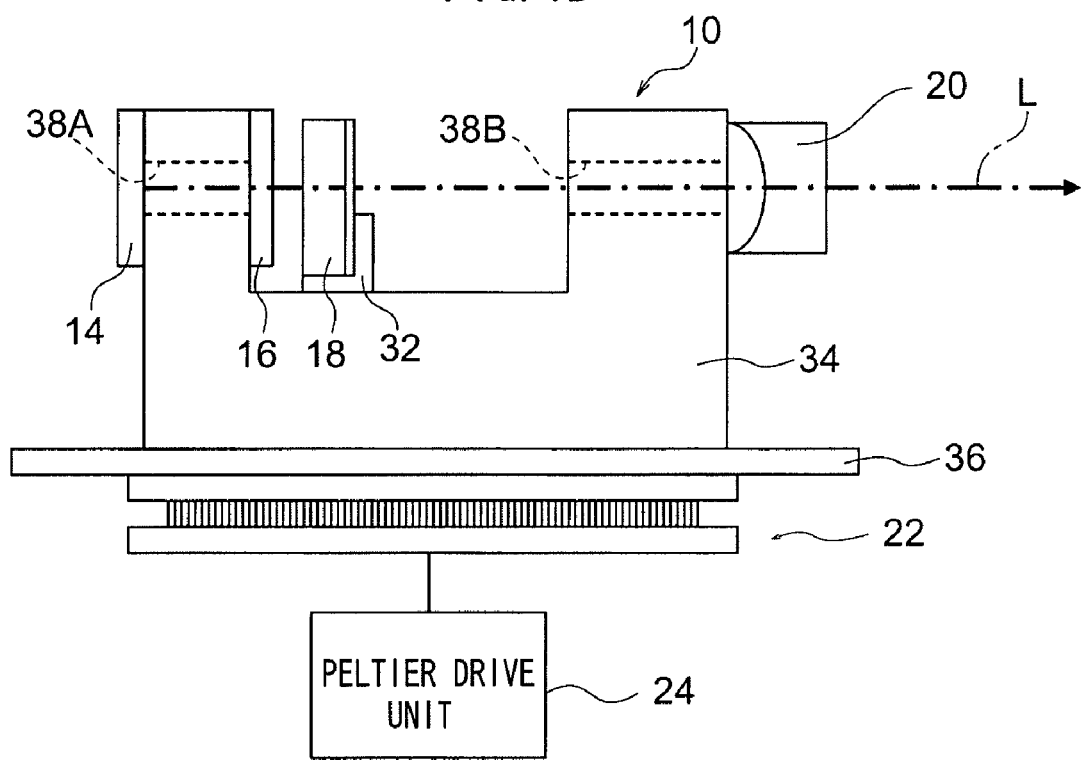
FIG. 1B is a schematic configuration diagram of a mode-locked laser device according to the first exemplary embodiment.

FIG. 1A is a schematic plan view of a mode-locked laser device 10, and FIG. 1B shows a schematic side view thereof. As shown in FIGS. 1A and 1B, the mode-locked laser device 10 is configured including: an excitation light optical system 12; a SESAM 14; a solid-state laser medium 16; a dichroic mirror 18; a resonance mirror 20; a Peltier device 22; and a Peltier drive unit 24.

As shown in FIG. 1A, the excitation light optical system 12 is configured including a semiconductor laser 26, serving as an excitation light source and a SELFOC lens 28, fixed, by for example adhesive, onto an excitation light optical system holder 30, configured by a component made from copper, for example.

A dichroic mirror holder 32, to which the SESAM 14, the solid-state laser medium 16, the resonance mirror 20, and the dichroic mirror 18 are attached, is fixed to a resonator holder 34, for example by adhesive. The excitation light optical system 12 is omitted in the view shown in FIG. 1B.

The resonator holder 34 is, as shown in FIG. 1B, of a substantially U-shape, formed with holes 38A, 38B for letting pulsed light L pass therethrough.

The resonator holder 34 has, for example, an overall length in the left-right direction of FIG. 1B of about 30 mm.

The excitation light optical system holder 30 and the resonator holder 34 are fixed onto a copper plate 36 shown in FIG. 1B.

The SESAM 14 is a Semiconductor Saturable Absorber Mirror, and, for example, one manufactured by BATOP GmbH, having a modulation depth ($\Delta R$) of 0.4% to light of wavelength 1064 nm, a non-saturable loss ($R_{ns}$) of 0.2%, and a saturation fluence of 70 µJ/cm$^2$ can be employed.

A resonator is configured by the SESAM 14 and the resonance mirror 20. Namely, the SESAM 14 makes common use of one of the pair of resonance mirrors configuring the resonator.

The solid-state laser medium 16 is, for example, a medium formed from Nd:YVO$_4$, and one with a thickness of 1 mm and Nd concentration of 2% can be employed. Both end faces of the solid-state laser medium 16 are treated with an anti-reflection coating, to give a transmittance of 95% or greater to light of wavelength 808±5 nm, and a transmittance of 99.9% or greater to light of wavelength 1064±10 nm.

The solid-state laser medium 16 is fixed to the resonator holder 34 so as to be positioned adjacent to the end face of the SESAM 14, about 1 mm away, so that the diameter of the oscillating beam therein is small.

The dichroic mirror 18 reflects excitation light from the excitation light optical system 12 toward the solid-state laser medium 16. One end face of the dichroic mirror 18 is treated with a dichroic coating having a reflectance of 95% or greater to light of wavelength 808±5 nm, and a transmittance of 99.9% or greater to light of wavelength 1064±10 nm, and the other end face is not treated with a coating.

The dichroic mirror 18 fixed to the dichroic mirror holder 32 is disposed within the resonator between the SESAM 14 and the resonance mirror 20, so as to form a Brewster angle to the resonator optical axis.

The resonance mirror 20 is a concave mirror with, for example, a 30 mm radius of curvature, and, for example, is fixed to the resonator holder 34 so as to be disposed at a position about 30 mm from the end face of the SESAM 14. The concave side of the resonance mirror 20 is treated with a high reflection coating of reflectance of 99.8% or greater to light of wavelength 1064±5 nm.

For the semiconductor laser 26 of the excitation light optical system 12, for example, one having a wavelength of 808 nm, emitted beam width of 50 μm, and maximum output of 1.5 W can be employed, such as one manufactured by Axcel Photonics Inc.

For the SELFOC lens 28 of the excitation light optical system 12, for example, one having a length of 5.4 mm and a diameter of 1.8 mm, can be employed, with anti-reflection coating treatment to light of 808 nm performed to both end faces.

The Peltier device 22 is installed to the copper plate 36, which in turn has the resonator holder 34 and the excitation light optical system holder 30 attached thereto, the resonator holder 34 having the SESAM 14, the solid-state laser medium 16, the resonance mirror 20 and the dichroic mirror holder 32 fixed thereon.

The resonator holder 34 and the excitation light optical system holder 30 are adjusted in temperature with the Peltier device 22. The Peltier device 22 is driven by the Peltier drive unit 24.

Consequently, since the resonator holder 34 is adjustable in temperature, the resonator length can be changed, and the pulse repetition rate of the pulsed light L output from the resonator can be adjusted. Also, since the excitation light optical system holder 30 is temperature adjustable, the semiconductor laser 26 the can be adjusted to a temperature enabling stable oscillation.

Since configuration is made with the SESAM 14, the solid-state laser medium 16, the resonance mirror 20, and the dichroic mirror holder 32 fixed to the single resonator holder 34, there is no need to separately prepare a holder for each of the components, a simple and compact configuration can be made, and the device can be manufactured at low cost.

The inventors have confirmed that an ultra short pulse light of 1064 nm wavelength, with pulse repetition rate 4.7873 GHz, average output 70 mW, and pulse width 6 ps can be obtained with the mode-locked laser device 10 configured as above. Namely, it has been confirmed that the mode-locked laser device 10 according to the present exemplary embodiment functions as a picosecond pulse laser.

Figure 2:
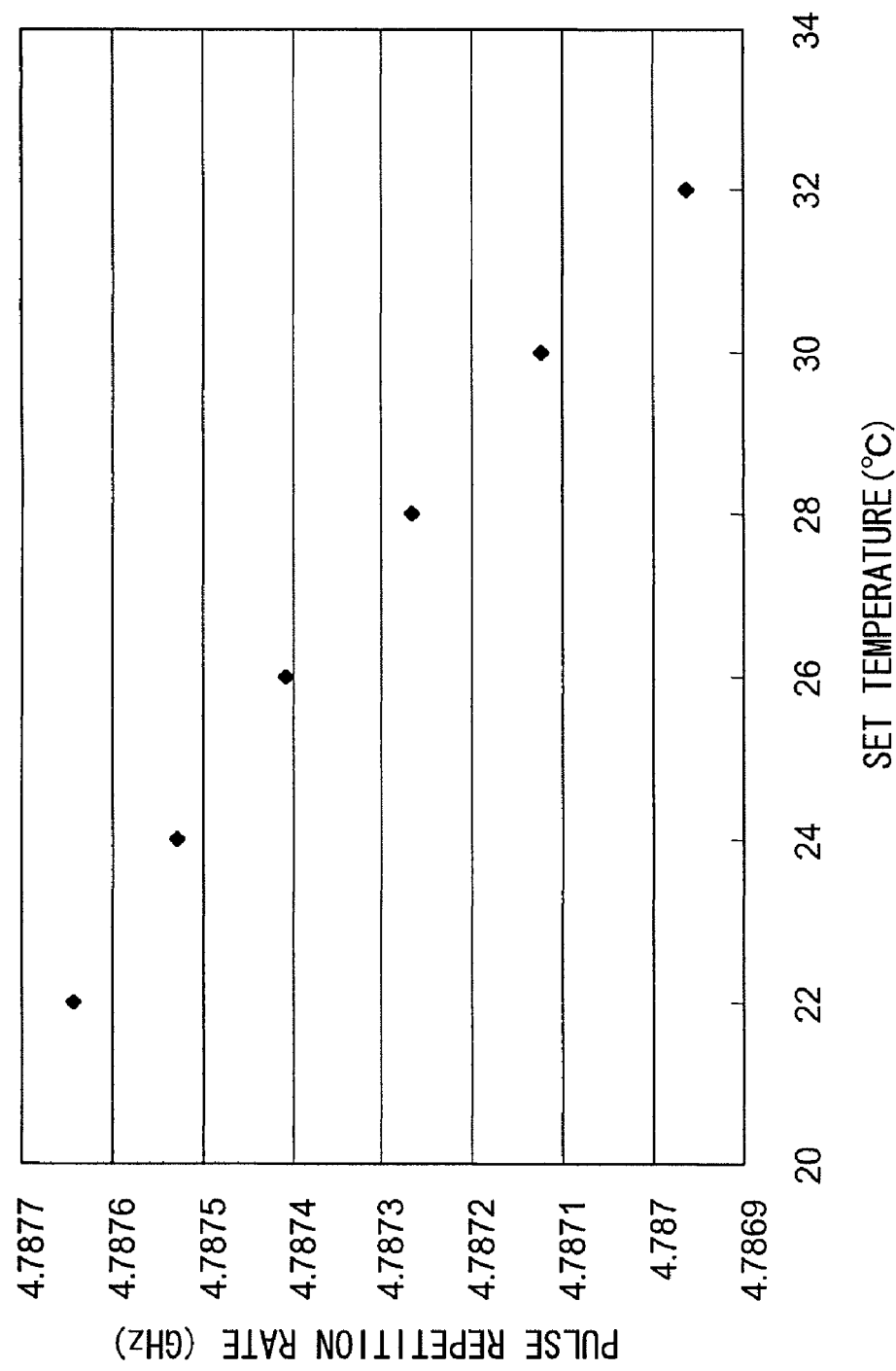
FIG. 2 is a graph showing the relationship between the temperature of a resonator holder and the pulse repetition rate of a mode-locked laser device according to the first exemplary embodiment.

In addition, as shown in FIG. 2, it has been confirmed that the pulse repetition rate can be varied from about 4.7877 GHz to 4.7870 GHz by changing the temperature of the resonator holder 34 from 22° C. to 32° C. using the Peltier drive unit 24.

Consequently, the resonator holder 34 can readily adjust the pulse repetition rate by driving the Peltier device 22 using the Peltier drive unit 24 such that the temperature corresponds to that of the desired pulse repetition rate.

A temperature sensor, such as a thermistor, is preferably attached to the resonator holder 34, and the Peltier device 22 driven so that the temperature detected by the temperature sensor attains the temperature corresponding to the desired pulse repetition rate.

Figure 3A:
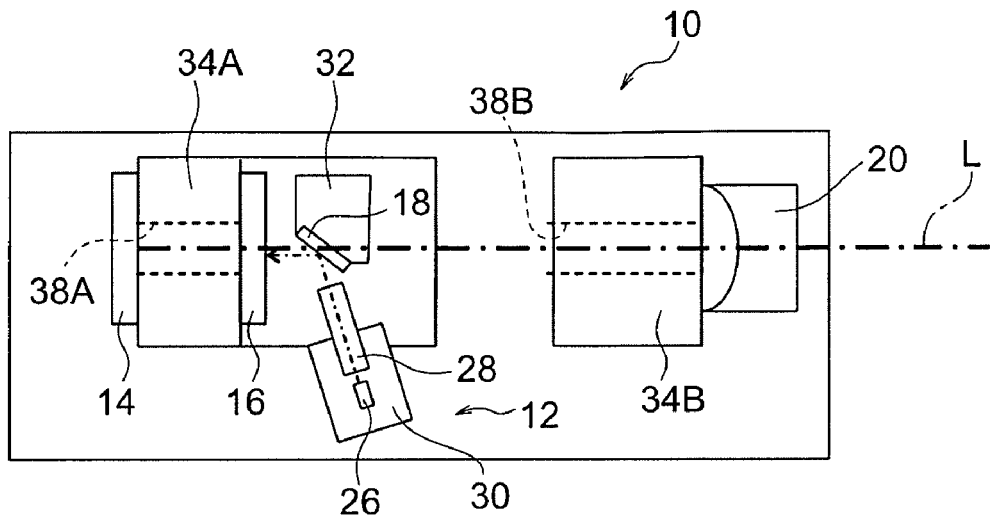
FIG. 3A is a schematic configuration diagram showing a modified example of a mode-locked laser device according to the first exemplary embodiment.
Figure 3B:
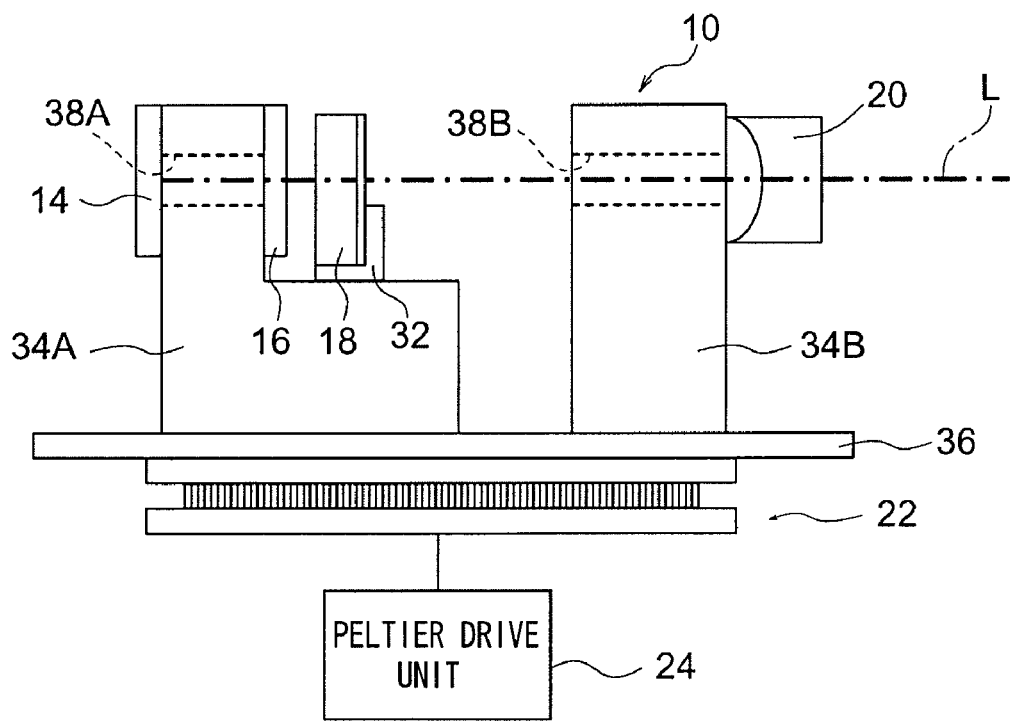
FIG. 3B is a schematic configuration diagram showing a modified example of a mode-locked laser device according to the first exemplary embodiment.

In the present exemplary embodiment, explanation has been given of a configuration in which each of the optical elements are fixed to the same resonator holder 34, however there is no limitation thereto, and configuration may be made with the optical elements attached to plural holders. For example, as shown in FIGS. 3A and 3B, the resonator holder 34 may be configured with a first resonator holder 34A, for fixing the SESAM 14, the solid-state laser medium 16 and the dichroic mirror holder 32, and a second resonator holder 34B, for fixing the resonance mirror 20.

Second Exemplary Embodiment

Explanation will now be given of the second exemplary embodiment of the present invention. Similar parts of the configuration to those of the first exemplary embodiment are allocated the same reference numerals and detailed explanation thereof is omitted.

Figure 4A:
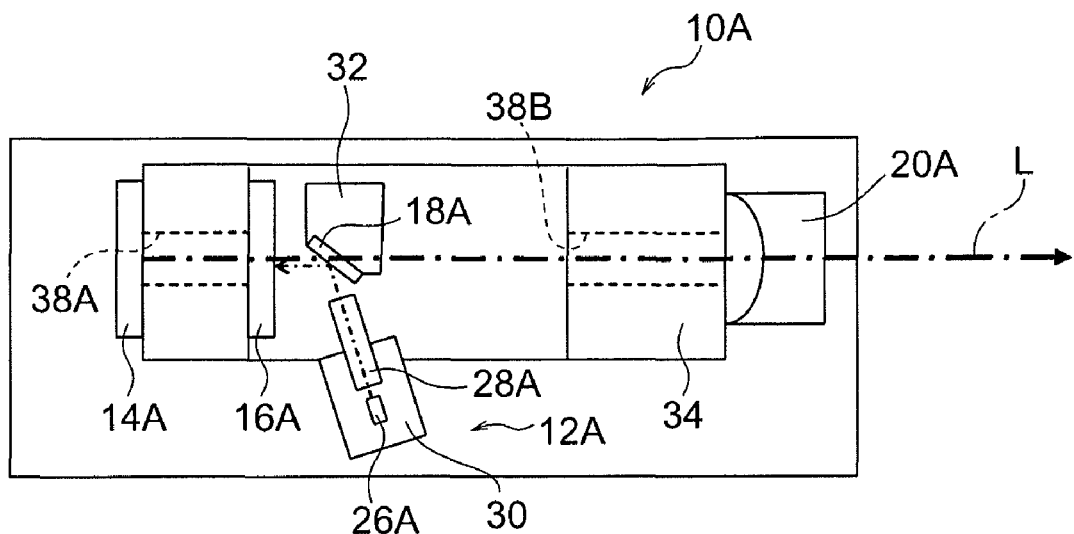
FIG. 4A is a schematic configuration diagram of a mode-locked laser device according to a second exemplary embodiment.
Figure 4B:
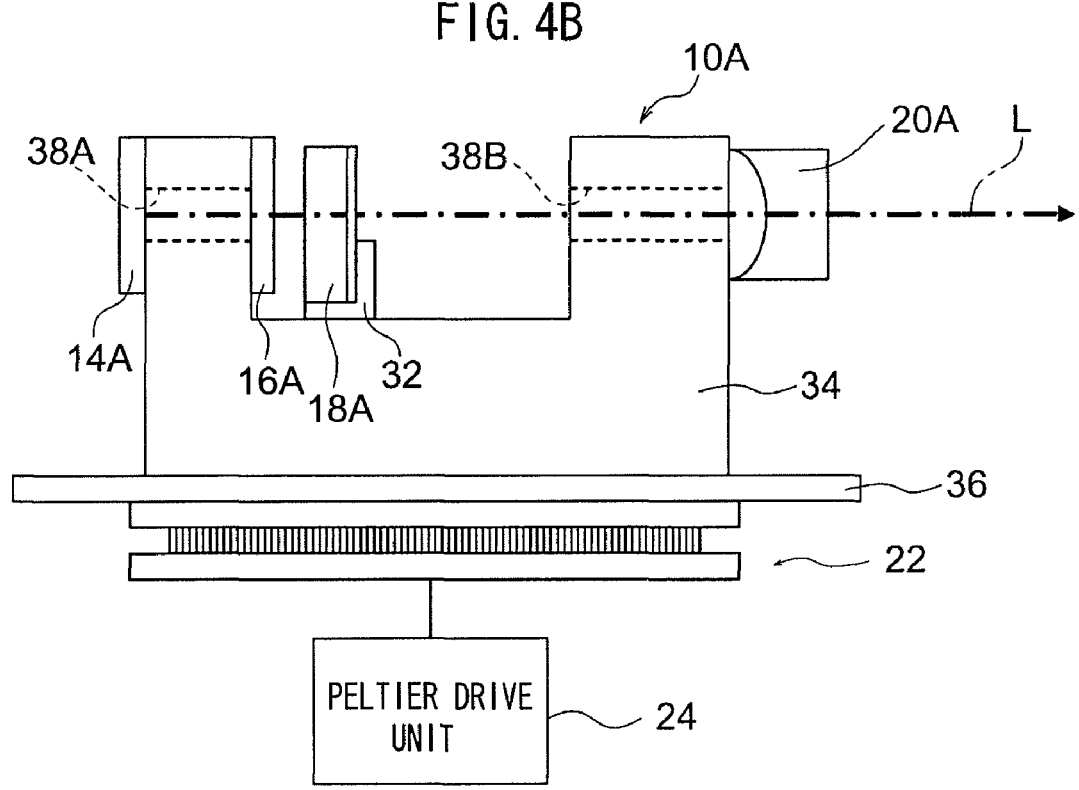
FIG. 4B is a schematic configuration diagram of a mode-locked laser device according to the second exemplary embodiment.

FIGS. 4A and 4B show a schematic configuration of a mode-locked laser device 10A according to the second exemplary embodiment of the present invention. The mode-locked laser device 10A is of substantially the same configuration to that of the mode-locked laser device 10. Since only the characteristics of some of the optical elements differ the optical elements with different characteristics will be allocated a different reference number, and the other optical elements will be allocate the same reference numerals and explanation thereof omitted.

As the SESAM 14A, for example, one manufactured by BATOP GmbH, having a modulation depth (ΔR) of 0.5% to light of wavelength 1045 nm, a non-saturable loss ($R_{ns}$) of 0.2%, and a saturation fluence of 70 μJ/cm² can be employed.

A solid-state laser medium 16A is, for example, a medium formed from Yb:KYW, and one with a thickness of 1.5 mm, and Yb concentration of 5% can be employed. Both end faces of the solid-state laser medium 16A are treated with an anti-reflection coating, to give a transmittance of 95% or greater to light of wavelength 980±5 nm, and of 99.9% or greater to light of wavelength 1045±10 nm.

The solid-state laser medium 16A is fixed to a resonator holder 34 so as to be positioned adjacent to the end face of the SESAM 14A, about 1 mm away, so that the diameter of the oscillating beam therein is small.

A dichroic mirror 18 reflects excitation light from a excitation light optical system 12A toward the solid-state laser medium 16A. One end face of the dichroic mirror 18A is treated with a dichroic coating having a reflectance of 95% or greater to light of wavelength 980±5 nm, and a transmittance of 99.9% or greater to light of wavelength 1045±10 nm, and the other end face is not treated with a coating.

A semiconductor laser with, for example, wavelength 980 nm, spectral width 50 μm, and maximum output 2.5 W made by, for example, Optoenergy Inc. can be used as a semiconductor laser 26A.

A SELFOC lens 28A is 5.4 mm long, has a diameter of 1.8 mm, and has anti-reflection coating treatment of both end faces to light of 980 nm wavelength.

A resonance mirror 20A is a concave mirror of 50 mm radius of curvature, and is fixed to the resonator holder 34 so as to be disposed about 50 mm from the end face of the SESAM 14A. The concave side of the resonance mirror 20A is treated with a partially transmitting negative dispersion coating of transmittance 1.8% to light of wavelength 1045±5 nm, and a group velocity dispersion of $-800$ fs$^2$.

By using the resonance mirror 20A treated with the special coating, a special mode-locked state is induced in the resonator, called a soliton mode locking, and a small femtosecond laser is obtained that is compact, having a resonator length 50 mm, and is capable of outputting an ultra short pulse with a pulse width of the order of a few hundred fs.

The inventors have confirmed that an ultra short pulse of wavelength 1045 nm, with a pulse repetition rate of 2.85 GHz, average output of 700 mW, and pulse width of 220 fs, can be obtained with the mode-locked laser device 10A configured as described above.

Figure 5:
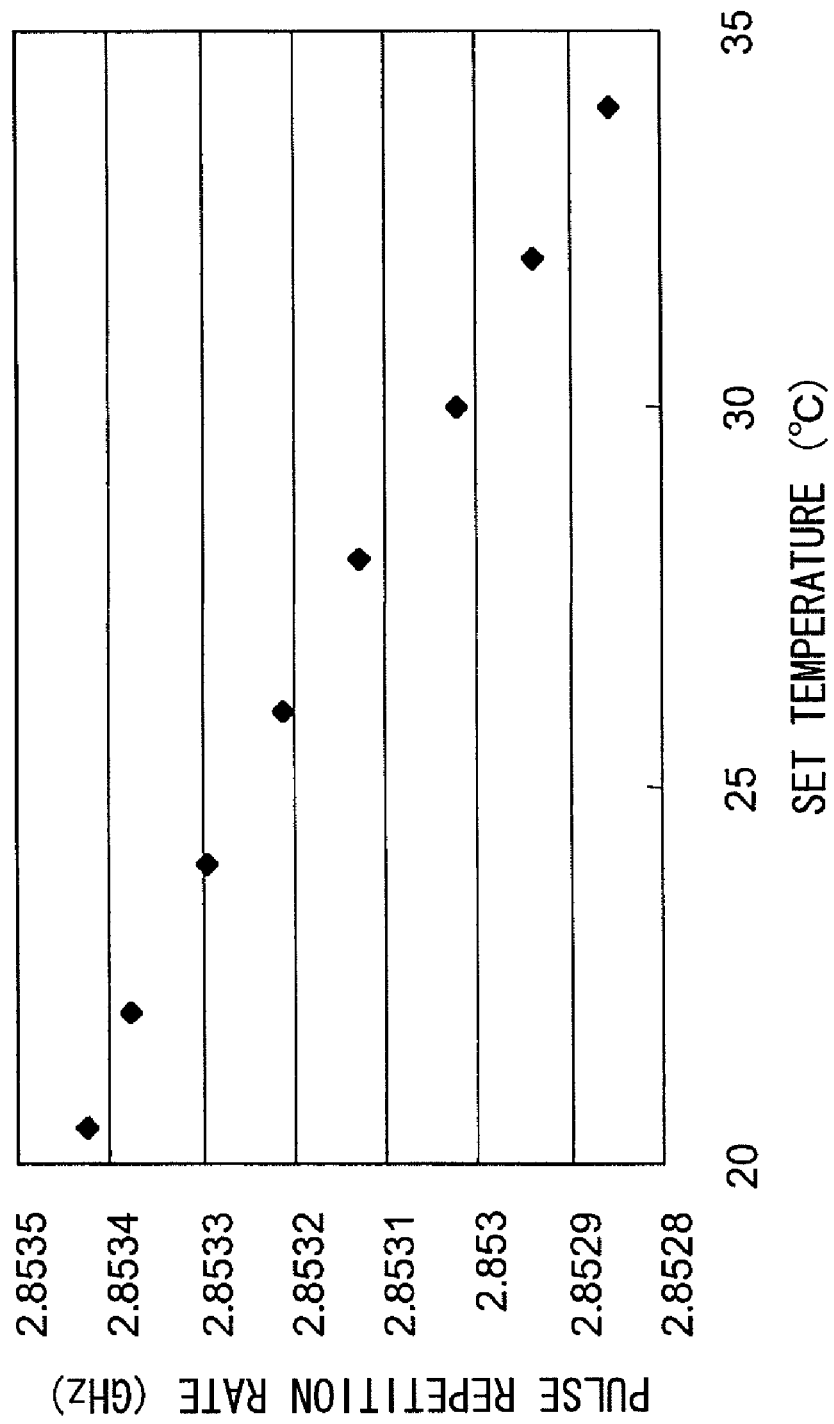
FIG. 5 is a graph showing the relationship between the temperature of a resonator holder and the pulse repetition rate of a mode-locked laser device according to the second exemplary embodiment.

In addition, as shown in FIG. 5, confirmation has been made that the pulse repetition rate can be varied from about 2.8534 GHz to about 2.8529 GHz by changing the temperature of the resonator holder 34 from 21° C. to 34° C. using the Peltier drive unit 24.

Third Exemplary Embodiment

Explanation will now be given regarding a third exemplary embodiment of the present invention. Similar parts of the configuration to those of the above exemplary embodiments are allocated the same reference numerals and detailed explanation thereof is omitted.

Figure 6A:
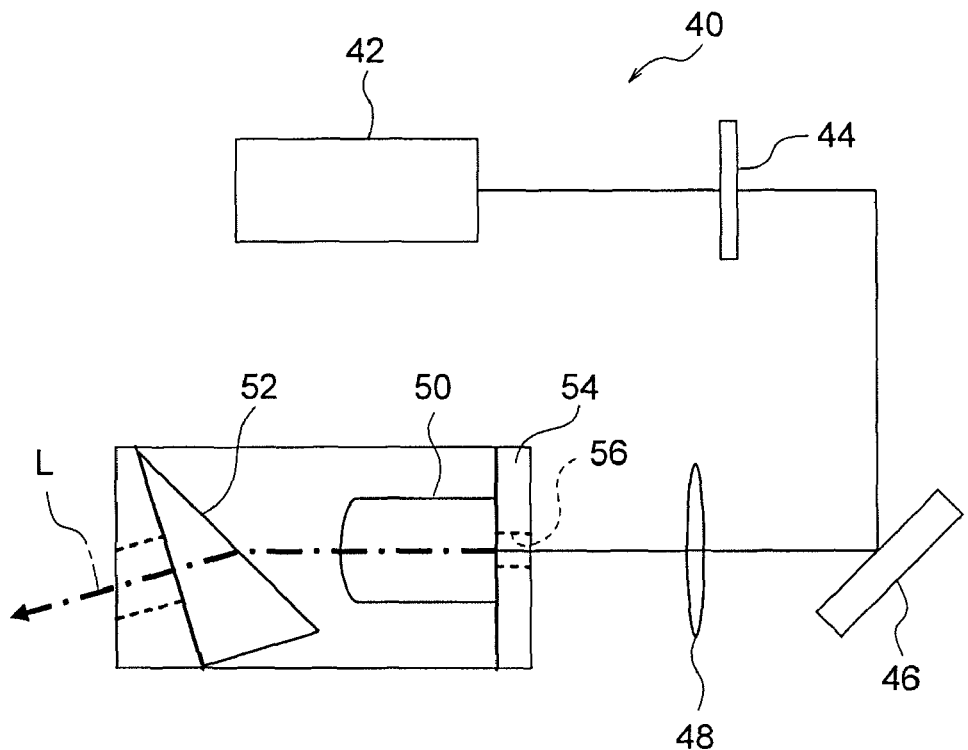
FIG. 6A is a schematic configuration diagram of a mode-locked laser device according to a third exemplary embodiment.
Figure 6B:
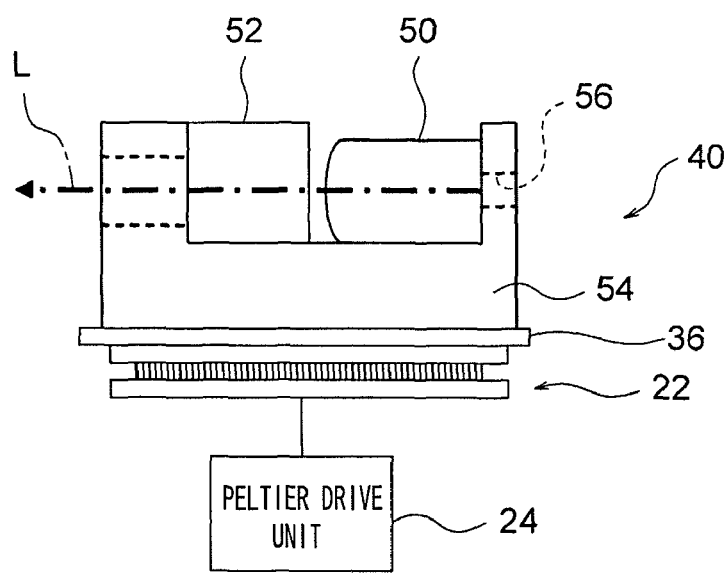
FIG. 6B is a schematic configuration diagram of a mode-locked laser device according to the third exemplary embodiment.

FIG. 6A is a schematic plan view of a mode-locked laser device 40 according to a third exemplary embodiment of the present invention, and FIG. 6B is a schematic side view thereof.

As shown in FIG. 6A, the mode-locked laser device 40 is configured including: a energizing light source 42; a λ/2 plate 44; a mirror 46; a lens 48; a solid-state laser medium 50; a Littrow Prism 52; a Peltier device 22; and a Peltier drive unit 24.

A Nd:YVO$_4$ laser (for example MILLENNIA IR, made by Spectra-Physics Co.) can, for example, be employed for the energizing light source 42.

The laser light output from the energizing light source 42 is polarized by the λ/2 plate 44, and reflected by the mirror 46 in the direction toward the lens 48. The laser light converged by the lens 48 is then introduced through a hole 56 provided in a resonator holder 54, to which the solid-state laser medium 50 and the Littrow Prism 52 are fixed.

The solid-state laser medium 50 is, for example, a medium formed from Cr:YAG, with a length of 18.3 mm and an absorption coefficient of 1.4 cm$^{-1}$ to light of 1064 nm wavelength.

One end face of the solid-state laser medium 50 is treated with a dichroic coating having a reflectance of 99.9% or above to light of 1525 nm wavelength, and a transmittance of 95% or above to light of 1064 nm wavelength, and the other end face thereof is a spherical surface of 6 mm radius of curvature, treated with an anti-reflection coating with transmittance of 99.99% or above to light of 1525 nm wavelength.

One end face of the Littrow Prism 52 is treated with a high reflectance coating having a reflectance of 99.5% or above to light of 1525 nm wavelength, and the other end thereof is treated with an anti-reflection coating having a transmittance of 99.9% or above to light of 1525 nm wavelength.

The group velocity dispersion within the resonator is controllable with the Littrow Prism 52, and the Littrow Prism 52 is disposed angled with respect to the resonator optical axis such that the group velocity dispersion within the resonator is $-500$ fs$^2$.

The resonator is configured with the solid-state laser medium 50 and the Littrow Prism 52 as described above. The solid-state laser medium 50 is a medium formed from Cr:YAG, inducing an optical Kerr effect. Consequently the mode-locked laser device 40 is a Kerr lens mode-locked laser device.

The inventors have confirmed that an ultra short pulse light of 1540 nm wavelength, with pulse repetition rate 2.64 GHz, average output 150 mW, pulse width 150 fs, can be obtained with the mode-locked laser device 40 configured as above.

Figure 7:
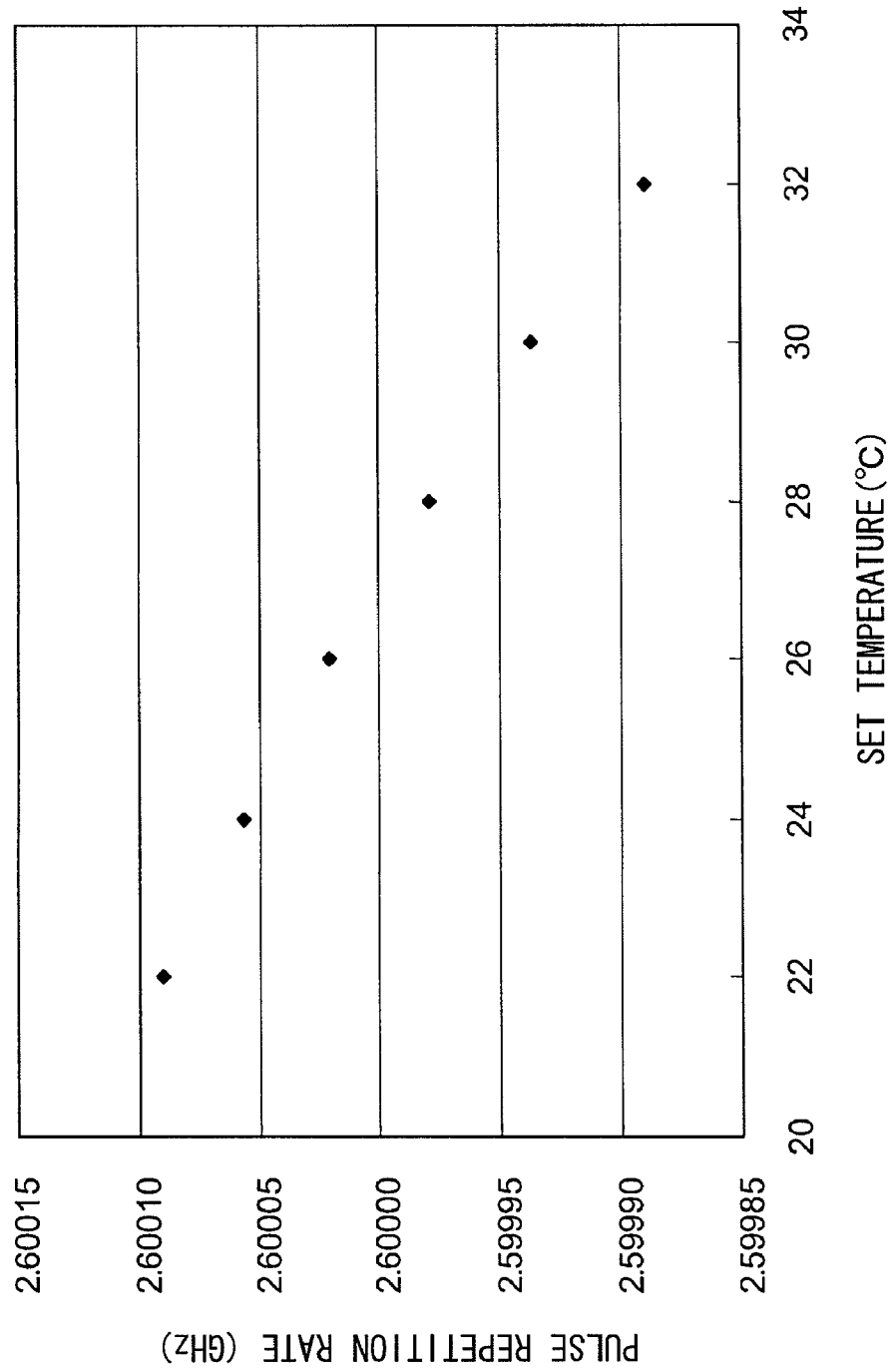
FIG. 7 is a graph showing the relationship between the temperature of a resonator holder and the pulse repetition rate of a mode-locked laser device according to the third exemplary embodiment.

Confirmation was also made, as shown in FIG. 7, that the pulse repetition rate could be adjusted from about 2.6001 GHz to 2.5999 GHz by changing the temperature of the resonator holder from 22° C. to 32° C. using the Peltier drive unit 24.

Fourth Exemplary Embodiment

Explanation will now be given of a fourth exemplary embodiment of the present invention. Similar parts of the configuration to those of the above exemplary embodiments are allocated the same reference numerals and detailed explanation thereof is omitted.

Figure 8:
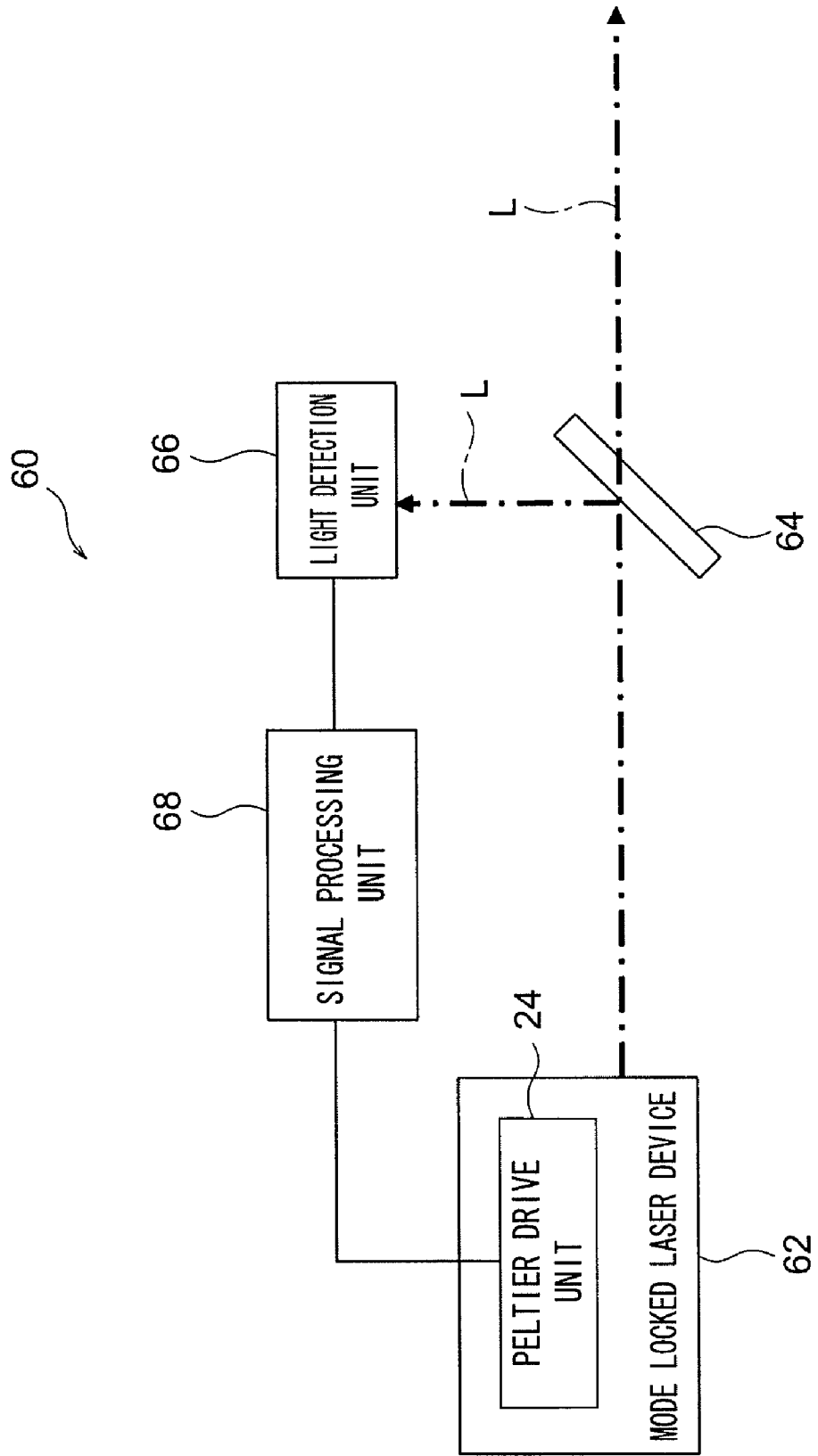
FIG. 8 is a schematic configuration diagram of a pulsed laser light source device according to a fourth exemplary embodiment.

FIG. 8 shows schematic configuration of a pulse laser light source device 60 according to a fourth exemplary embodiment of the present invention.

The pulse laser light source device 60 is configured including a mode-locked laser device 62, a beam splitter 64, a light detection unit 66, and a signal processing unit 68.

Any one of the mode-locked laser devices 10, 10A, 50 explained in the first to the third exemplary embodiments above can be employed as the mode-locked laser device 62.

A portion of the pulsed light L output from the mode-locked laser device 62 is split by the beam splitter 64 and detected by the light detection unit 66. The signal detected by the light detection unit 66 is signal-processed by the signal processing unit 68. This signal processing determines the deviation between the pulse repetition rate of the pulse light detected and a desired standard frequency, and is processing to output to the Peltier drive unit 24 of the mode-locked laser device 62 a control signal to minimize the deviation.

The Peltier drive unit 24 drives the Peltier device 22 such that a current according to the control signal flows in the Peltier device 22 of the mode-locked laser device 62. The temperature of the resonator holder of the mode-locked laser device 62 is thereby changed, and the pulse repetition rate of the pulsed light L matched to the desired pulse repetition rate.

By monitoring the pulse repetition rate of the pulsed light in this manner, the pulse repetition rate can be stabilized by feedback control.

The inventors have confirmed that the pulse repetition rate can be stabilized with a precision of ±10 kHz or less with respect to a standard frequency of 4.7873 GHz with the pulse laser light source device 60 employing the mode-locked laser device 10 as explained in the first exemplary embodiment.

The inventors have also confirmed that the pulse repetition rate can be stabilized with a precision of ±50 kHz or less with respect to a standard frequency of 2.8531 GHz with the pulse laser light source device 60 employing the mode-locked laser device 10A as explained in the second exemplary embodiment.

In addition, the inventors have confirmed that the pulse repetition rate can be stabilized with a precision of ±10 kHz or less with respect to a standard frequency of 2.6 GHz with the pulse laser light source device 60 employing the mode-locked laser device 50 as explained in the second exemplary embodiment.

Fifth Exemplary Embodiment

Explanation will now be given regarding a fifth exemplary embodiment of the present invention. Similar parts of the configuration to those of the above exemplary embodiments are allocated the same reference numerals and detailed explanation thereof is omitted.

Figure 9:
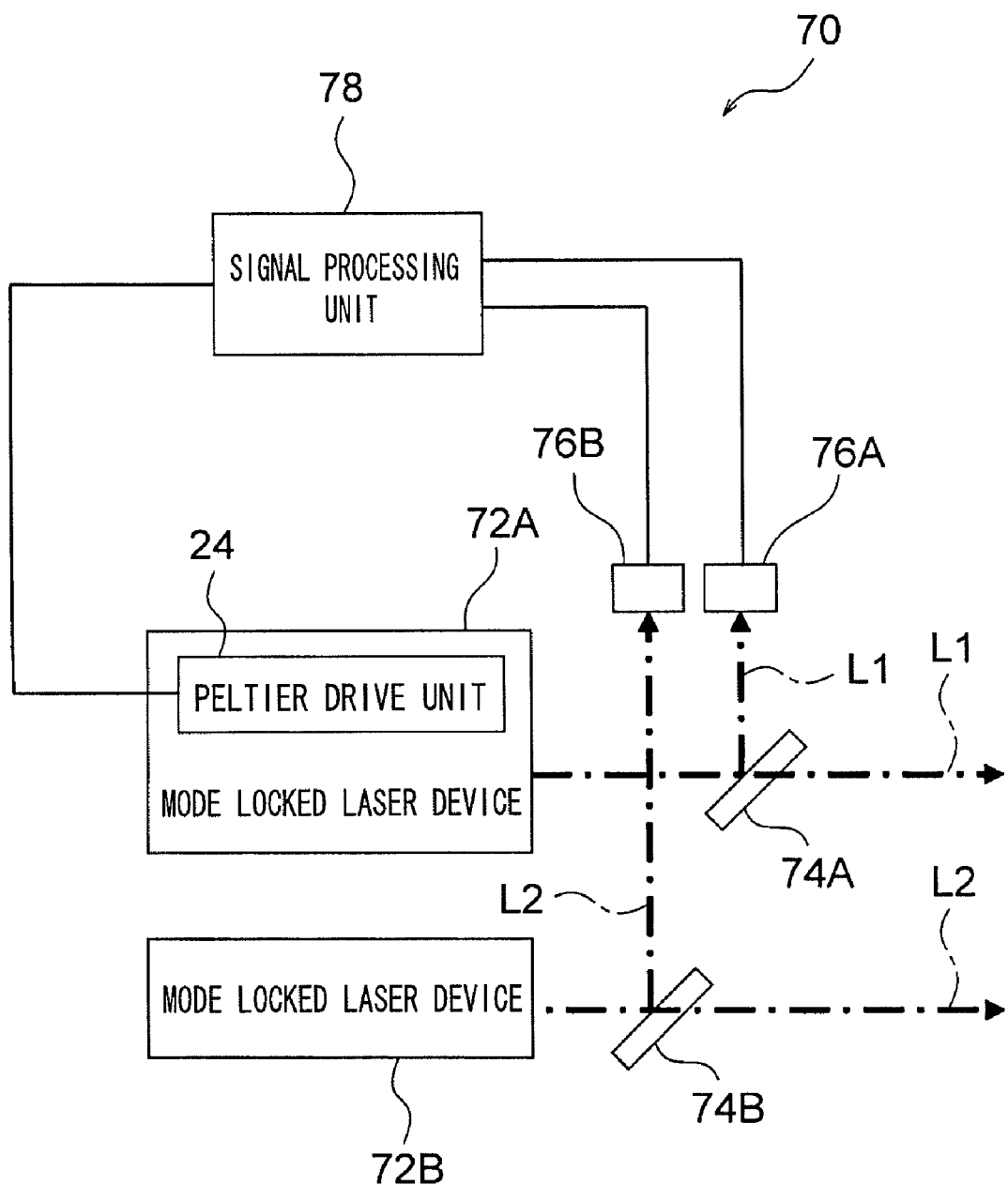
FIG. 9 is a schematic configuration diagram of a pulsed laser light source device according to a fifth exemplary embodiment.

FIG. 9 shows a schematic configuration of a pulse laser light source device 70 according to a fifth exemplary embodiment of the present invention.

As shown in FIG. 9, the pulse laser light source device 70 is configured including two mode-locked laser devices 72A, 72B, two beam splitters 74A, 74B, two light detection units 76A, 76B and a signal processing unit 78.

The solid-state laser medium 50 explained in the third exemplary embodiment can be employed, for example, as the mode-locked laser device 72A, and the mode-locked laser device 10 explained in the first exemplary embodiment can be employed, for example, as the mode-locked laser device 72B.

In the mode-locked laser device 72A the length of the resonator holder and the radius of curvature of the resonance mirror is adjusted such that the center of the pulse repetition rate is at 2.8531 GHz. Portions of the pulsed light L1, L2 output from the mode-locked laser devices 72A, 72B are split by the beam splitters 74A, 74B and detected by respective light detection units 76A, 76B.

The pulse light detected by the light detection units 76A, 76B is signal-processed by the signal processing unit 78. The signal processing unit 78 determines the deviation (relative jitter) between the pulse separations of the two detected pulse lights, and outputs to the Peltier drive unit 24 of the mode-locked laser device 72A a control signal to minimized the deviation.

The Peltier drive unit 24 is, for example, connected to a Peltier device 22 of the mode-locked laser device 72A, and the Peltier drive unit 24 drives the Peltier device 22 such that an electrical current flows in the Peltier device according to the control signal output from the signal processing unit 78, adjusting the temperature of the resonator holder 34. The length of the resonator is thereby changed, and the pulse light of the temperature adjusted mode-locked laser device 72A is synchronized to the pulse light of the other mode-locked laser device 72B.

The inventors have confirmed that according to the pulse laser light source device 70 configured as above, the relative jitter of the pulse lights output from the two mode-locked laser devices 72A, 72B can be suppressed to 500 fs or less.

Sixth Exemplary Embodiment

Explanation will now be given regarding a sixth exemplary embodiment of the present invention. Similar parts of the configuration to those of the above exemplary embodiments are allocated the same reference numerals and detailed explanation thereof is omitted.

Figure 10:
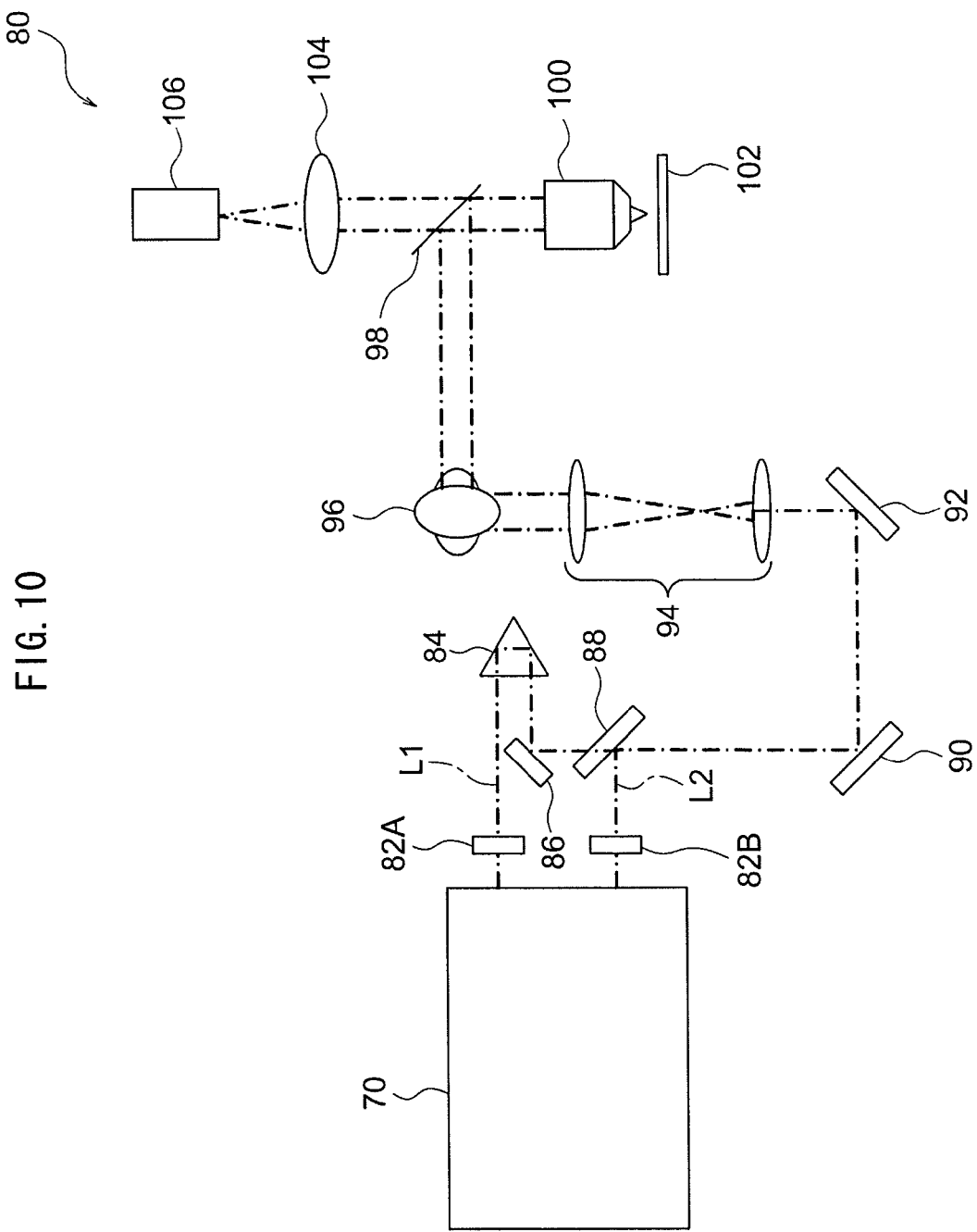
FIG. 10 is a schematic configuration diagram of a microscope device according to the sixth exemplary embodiment.

FIG. 10 shows a schematic configuration of a microscope device 80 according to a sixth exemplary embodiment of the present invention. As shown in FIG. 10, the microscope device 80 is a microscope device employing coherent anti-Stokes Raman scattering, and is equipped with the pulse laser light source device 70 explained in the fifth exemplary embodiment.

The two locked pulsed lights L1, L2 output from the pulse laser light source device 70 are modulated by the output modulation mechanisms 82A, 82B. A reflector prism 84 is provided on the optical axis of the pulse light L1. The reflector prism 84 has functionality for correcting any optical path difference between the two pulse lights.

The pulsed light L1 is then reflected toward the direction of a dichroic mirror 88 by a mirror 86. The pulsed light L1 and the pulsed light L2 are introduced by the dichroic mirror 88 into a beam expander optical system 94 by mirrors 90, 92 on the same optical axis.

Each of the pulse lights are then transmitted through the beam expander optical system 94 and a galvanometer mirror 96, reflected in the direction of an object lens 100 by a dichroic mirror 98, and the light that has been transmitted through the object lens 100 is converged at a specimen on a movable stage 102. Fluorescent light emitted from this specimen, after passing through the object lens 100 and the dichroic mirror 98, is converged by a condenser lens 104 at a PMT (photomultiplier: photoelectric multiplier tube) 106 and detected.

By using the pulse laser light source device 70, the overall size of the microscope device 80 employing coherent anti-Stokes Raman scattering can be made smaller. In addition, a large reduction in cost is possible in comparison to a microscope device using a conventional timing locked pulse laser light source device.

Note that while explanation has been given in the above exemplary embodiments of cases in which the resonance holder is adjusted in temperature by a Peltier device, the temperature adjusting unit is not limited to a Peltier device. There is also no limitation to adjusting the temperature of the resonance holder to which the resonance mirrors are fixed, and the resonance mirrors may be adjusted in temperature directly.

What is claimed is:

1. A mode-locked laser comprising:
    a resonator having a pair of resonance mirrors;
    a solid-state laser medium, disposed in the resonator and outputting oscillating light due to excitation light being incident thereon;
    an excitation unit that causes the excitation light to be incident on the solid-state laser medium;
    a mode-locked element, disposed in the resonator for inducing mode locking; and
    a temperature adjusting unit that adjusts the temperature of the pair of resonance mirrors such that oscillating light of a specific frequency is output from the resonator, wherein:
    the pair of resonance mirrors are retained by a retaining member that is the same retaining member for both of the pair of resonance mirrors; and
    the temperature adjusting unit adjusts the temperature of the retaining member.

2. The mode-locked laser of claim 1, wherein the mode-locked element is a semiconductor saturable absorber mirror device making common usage of one resonance mirror of the pair of resonance mirrors.

3. The mode-locked laser of claim 1, wherein:
    a group velocity dispersion compensation unit is provided in the resonator, the group velocity dispersion compensation unit controlling the group velocity dispersion in the resonator; and
    the resonator induces soliton mode locking.

4. The mode-locked laser of claim 1, wherein:

the mode-locked element is formed from a medium that induces an optical Kerr effect and makes common usage of the solid-state laser medium; and the resonator induces Kerr lens mode locking.

5. The mode-locked laser of claim 1, further comprising:

a pulse repetition rate detection unit that detects the pulse repetition rate of pulse light output from the resonator, wherein the temperature adjusting unit adjusts the temperature of the pair of resonance mirrors such that the difference between the pulse repetition rate detected by the pulse repetition rate detection unit and the specific pulse repetition rate is minimized.

6. A pulse laser light source device comprising:

a plurality of mode-locked laser devices; and a plurality of detecting units that detect respective pulse lights output from respective of the plurality of mode-locked laser devices, wherein each of the plurality of mode-locked laser devices comprises:

a resonator having a pair of resonance mirrors;

a solid-state laser medium, disposed in the resonator and outputting oscillating light due to excitation light being incident thereon;

an excitation unit that causes the excitation light to be incident on the solid-state laser medium;

a mode-locked element, disposed in the resonator for inducing mode locking; and a temperature adjusting unit that adjusts the temperature of the pair of resonance mirrors such that oscillating light of a specific frequency is output from the resonator, and wherein the temperature adjusting unit of at least one mode-locked laser device from the plurality of mode-locked laser devices adjusts the temperature of the pair of resonance mirrors such that a difference in pulse separation between the plurality of pulse lights detected by the plurality of detection units is minimized, wherein:

the pair of resonance mirrors are retained by a retaining member that is the same retaining member for both of the pair of resonance mirrors; and the temperature adjusting unit adjusts the temperature of the retaining member.

7. The pulsed laser light source device of claim 6, wherein the mode-locked element is a semiconductor saturable absorber mirror device making common usage of one resonance mirror of the pair of resonance mirrors.

8. The pulsed laser light source device of claim 6, wherein:

a group velocity dispersion compensation unit is provided in the resonator, the group velocity dispersion compensation unit controlling the group velocity dispersion in the resonator; and the resonator induces soliton mode locking.

9. The pulsed laser light source device of claim 6, wherein:

the mode-locked element is formed from a medium that induces an optical Kerr effect and makes common usage of the solid-state laser medium; and the resonator induces Kerr lens mode locking.

10. A microscope device comprising:

the pulsed laser light source device of claim 6;

an optical system that locks the plurality of pulse lights output from the pulsed laser light source device and irradiates the pulse lights onto a specimen; and a fluorescent light detection unit that detects fluorescent light from the specimen.

\* \* \* \* \*